United States Patent [19]

Soula et al.

[11] Patent Number: 5,914,098

[45] Date of Patent: Jun. 22, 1999

[54] AEROSOL COMPOSITION FOR FORMING A HYDRATED MEMBRANE, AND APPLICATIONS THEREOF

[75] Inventors: Gérard Soula, Meyzieu; Jean-Michel Grosselin; Rafaël Jorda, both of Lyons; Catherine Castan, Brignais, all of France

[73] Assignee: Flamel Technologies, Venissieux Cedex, France

[21] Appl. No.: 08/615,290

[22] PCT Filed: Sep. 27, 1994

[86] PCT No.: PCT/FR94/01123

§ 371 Date: May 10, 1996

§ 102(e) Date: May 10, 1996

[87] PCT Pub. No.: WO95/08984

PCT Pub. Date: Apr. 6, 1995

[30] Foreign Application Priority Data

Sep. 28, 1993 [FR] France .................................. 93 11761

[51] Int. Cl.$^6$ ....................................................... A61K 9/12
[52] U.S. Cl. ............................ 424/45; 424/59; 424/443; 424/445; 424/78.05; 424/405; 424/DIG. 10; 514/937; 514/919; 514/834
[58] Field of Search ............................. 424/45, 484, 443, 424/445, 59, 78.05, 405, DIG. 10; 514/937, 919, 834

[56] References Cited

U.S. PATENT DOCUMENTS 4,920,158  4/1990  Murray et al. .

FOREIGN PATENT DOCUMENTS 0 327 411  8/1989  European Pat. Off. .
0 521 455  1/1993  European Pat. Off. .
0 560 014  9/1993  European Pat. Off. .

*Primary Examiner*—Raj Bawa
*Attorney, Agent, or Firm*—Bacon & Thomas, PLLC

[57] ABSTRACT

The present invention relates to an aerosol composition for forming a preferably hydrated membrane which after vaporizing comprises as least one hydrophobic phase containing at least one film-forming polymer at least partly solubilized in an organic solvent system. The polymer is selected from hydrophobic polyaminoacids, preferably from the polyaminoacids obtained from at least one of the amino acids alanine, valine, leucine, isoleucine, proline, methionine, phenylalanine, tryptophan, aspartic and glutamic acid esters, or the derivatives thereof. The compositions also comprises as least one hydrophilic phase, and at least one propellant. The preferably hydrated membrane formed by vaporizing this composition, the application of the composition and of the preferably hydrated membrane as a dressing, are also disclosed.

57 Claims, No Drawings

AEROSOL COMPOSITION FOR FORMING A HYDRATED MEMBRANE, AND APPLICATIONS THEREOF

This application is a 371 of PCT/FR94/01123 filed Sep. 27, 1994.

BACKGROUND OF THE INVENTION

1. Field of the Invention

The field of the present invention is that of aerosol compositions and more particularly those consisting of propelled film-forming substances which are useful especially, but not exclusively, for the application of a curative protective film to lesions, for example skin lesions.

More precisely, the present invention relates to an aerosol composition for forming a preferably hydrated membrane.

The invention further relates to the preferably hydrated membrane obtained from the abovementioned aerosol composition.

Without implying a limitation, the invention relates more specifically to the application of this aerosol composition and this preferably hydrated membrane for the dressing of wounds, burns or the like.

2. Description of the Prior Art

The purpose of dressing these local traumatisms, often on the skin, is to protect them from the external environment so as to avoid bacterial contamination and allow rapid healing of high quality. To this end, the dressing should obviously be biocompatible so as to be perfectly tolerated, and should preferably be transparent so that the condition and progress of the traumatism can be checked easily.

It is also advantageous for the dressing to possess a degree of mechanical strength, to be permeable to water vapor and also to be easy and painless to apply and remove.

The most traditional dressing is the one consisting of gauze (optionally mounted on adhesive plastic tape). The major disadvantage of this type of dressing is that it adheres too strongly to the wound, whereby the changes of dressing, which are of necessity relatively frequent, are delicate and painful operations. Moreover, the dressed lesions are in most cases suppurant, causing obstruction of the gauze or similar dressing. The dressing consequently becomes impermeable, thereby detracting from the healing and curing of the lesion.

Propelled film-forming substances for dressings are also known which consist of aerosol compositions comprising an active polymer as the film-forming substance, said polymer being capable of forming, after vaporization, a biocompatible film which adheres conveniently to the skin and is transparent and elastic, to name only some of the abovementioned properties expected for application as a dressing.

A wide variety of aerosol compositions containing a film-forming polymer have already been proposed. The following examples may be mentioned:

a composition containing polyvinyl acetate, polyvinylpyrrolidone and acetic acid (cf. FR-A-1 589 917), a composition based on curable polysiloxane, of the two-component type, associated with a propellant gas (cf. FR-A-2 589 737), a composition consisting of polyacrylates or methacrylates, ethyl cellulose, polyvinylbutyral, an ethylene oxide copolymer or a polyisobutylene in solution in solvent such as butanol (cf. FR-A-2 219 793 and FR-A-2 212 134), or else a composition containing an ammonium salt of organosilicon compounds bonded to organic polymers such as polyvinylpyrrolidone or cellulose acrylate or methacrylate, associated with a solvent propellant (cf. U.S. Pat. No. 4,921,691).

The constituent polymers of these known aerosol compositions have the disadvantage of producing non-hydrated films which are not entirely satisfactory in terms of healing. Moreover, it is clear that, in all probability, these polymers comprise unnatural residual monomers which are capable of generating inflammatory reactions on account of their toxicity towards a living medium (e.g. acrylic derivatives and siloxanes).

In an attempt to improve these vaporizable aerosol compositions for dressings, EP-A-0 521 455 has proposed replacing the known, imperfect film-forming polymers with a biodegradable hydroxycarboxylic acid polymer. The polymer in question can be a polylactic and/or polyglycolic polymer dissolved in a propellant solvent such as dimethyl ether, a freon, a gaseous alkane (e.g. liquefied propane) or an analog of said solvents. This aerosol composition also comprises water and an alcohol such as ethanol, which is useful as a solvent for various therapeutic active principles which may be present.

Despite the advantages of their biocompatibility and biodegradability, these hydroxycarboxylic acid polymers suffer from a serious shortcoming associated with the quality of the film they can produce after vaporization. In fact, it is found that the aerosol compositions based on these hydroxycarboxylic acid polymers are the center of a macroscopic phase separation during vaporization, the consequence of which is to eliminate the water to give a dry film. Such a product seems to be rather unsuitable for the dressing of wounds, burns or the like because its excessively anhydrous nature means that it either has difficulty adhering to the wound or adheres to it too strongly, which causes difficulties and pain when the film is detached.

There is therefore an obvious need for an aerosol composition based on a biocompatible, biodegradable and non-toxic polymer and pharmaceutically acceptable excipients which, on vaporization, can produce inter alia dressings in the form of films, the latter meeting specifications appropriate to this application:

cohesion, permeability to water vapor and oxygen, impermeability to bacteria, biocompatibility, tolerance and non-toxicity, healing promoter, analgesic, convenient adhesion to the damaged area, while remaining detachable with ease and without pain, and preferably a hydrated state which provides a degree of flexibility and a degree of elasticity and which accelerates the curing process (M. F. JONKMAN in "High Performance Biomaterials", Ed. M. Szycher, Technomic (1991)).

A solid form of dressing or temporary skin substitute is known which has all these properties; it is in the form of a flexible, translucent, colorless membrane marketed under the name INERPAN®. This skin substitute consists of a leucine/methyl glutamate copolymer impregnated with a liquid based on polyethylene glycol, sodium chloride and purified water.

Although INERPAN® has demonstrated perfectly its efficacy for the dressing of burns and bedsores in particular, it only exists in the form of thick membranes of predetermined dimensions. Moreover, the application of this dressing requires cautious manipulation and use, limiting its use in today's hospital environment.

It follows from the above that the development of a polymer formulation based on amino acids which formed a film on vaporization would be a totally desirable and valuable technical development, particularly in the field of human health and especially with a view to application as a dressing.

The spray form of a biocompatible, preferably hydrated membrane would represent a novel product, both in design and in realization, and would have the following advantages over the presently known, conventional, non-vaporizable dressings based on hydrogel membranes:

a low unit treatment cost because-of the small amount of product required per dressing, and substantial ease of use, which would make the product suitable for use by the general public, and variety and flexibility as regards the size of the dressings (surface area and thickness).

Consequently, one of the essential objectives of the invention is to provide a pharmaceutically acceptable aerosol composition for forming a hydrated membrane after vaporization, said membrane being usable especially as a dressing and possessing the properties referred to above, particularly those of a cohesive, preferably hydrated, biocompatible and therapeutically effective film. To achieve this and other objectives, the Applicant succeeded, after numerous experiments and studies, in solving the problem of which some of the aspects are as follows:

to render compatible a mixture of a hydrophobic phase containing a film-forming polymer, and a hydrophilic phase, so as to prevent precipitation of the polymer and allow simultaneous vaporization of these two phases to give a membrane, to give this membrane good cohesion, and preferably, to ensure that this membrane is suitably hydrated.

SUMMARY OF THE INVENTION

The solution to this problem consists particularly in producing the mixture of a hydrophobic phase containing the film-forming polymer, and a hydrophilic phase, and in selecting the film-forming polymer from polyamino acids.

DESCRIPTION OF THE PREFERRED EMBODIMENTS

The present invention thus relates to an aerosol composition for forming a preferably hydrated membrane after vaporization, characterized in that it comprises:

at least one hydrophobic phase containing a hydrophobic polyamino acid which is at least partially solubilized in an organic solvent system and is preferably selected from polyamino acids obtained from at least one of the following hydrophobic amino acids or derivatives: alanine, valine, leucine, isoleucine, proline, methionine, phenylalanine, tryptophan and aspartic and glutamic acid esters, at least one, preferably aqueous, hydrophilic phase, and at least one propellant.

Such an aerosol composition is particularly advantageous as a dressing since, on the one hand, it is easy and painless to apply to the lesion and, on the other hand, the film obtained after spraying contains at least one hydrophilic product and/or at least one liquid and/or retains the water initially present, at least for a few minutes, so that a preferably hydrated membrane forms.

This preferably hydrated polymer film is non-toxic and non-irritant and may be transparent. It favors healing and is easy and painless to detach from the lesion.

These results are particularly surprising and unexpected insofar as the structural polyamino acid(s) contained in the hydrophobic phase is (are) incompatible with the aqueous phase or with other components of the composition, such as the propellant. It was therefore difficult to imagine a priori:

1—how to vaporize both the hydrophobic and hydrophilic phases simultaneously,

2—how to obtain a cohesive film rather than a mass of individual particles, and

3—how the polymer could trap the water after vaporization and evaporation of the solvent.

Yet it is found that simple shaking of the polyphase mixture according to the invention gives an emulsion which, after vaporization, produces a moist, cohesive and homogeneous film. Contrary to all expectations, this emulsion does not require the incorporation of surfactants; furthermore, no precipitation of the polymer is observed. It is self-evident that the invention is not thereby limited to compositions without surfactants. It is indeed possible for the latter to be adjuvants in said compositions.

The polyamino acid selected according to the invention can be a homopolymer or a copolymer of hydrophobic amino acids preferably selected from those mentioned above. In the present disclosure, these homopolymers and copolymers will be referred to indiscriminately by the term polymer.

In one advantageous modality of the invention, the content of hydrophobic amino acids in the polyamino acid is greater than or equal to 5% by number and preferably greater than or equal to 15% by number.

These polymers have a sufficient molecular weight to give the body and texture of a membrane to the materials obtained by vaporization of the aerosol composition of the invention. As a general indication, this molecular weight can vary approximately from $10^3$ to $15 \times 10^5$ and preferably from $4 \times 10^4$ to $3 \times 10^5$ D.

Polymers of leucine and/or glutamic acid alkyl esters (preferably methyl, ethyl or benzyl esters) are preferentially chosen as the polyamino acid. In the case of a copolymer, for example Leu/Glu(OMe), the respective relative proportions, expressed in mol, are between 99/1 and 1/99, preferably between 30/70 and 70/30 and particularly preferably between 45/55 and 55/45.

According to the invention, the aerosol composition can comprise a single polymer or a mixture of polymers.

As far as the synthesis of these polymers is concerned, it should be stated that it is perfectly known per se. Thus, for example, the polymers used in the composition of the invention can be those described in the following patent applications: GB 996 760 and FR 1 603 159.

The polymer or polymers are present in the aerosol composition in an amount of 0.05 to 30% by weight/weight, based on the total amount of aerosol.

Expressed differently, the concentration of the polymer in the hydrophobic organic phase is between 0.1 and 40, preferably between 0.5 and 10 and particularly preferably between 0.5 and 4% by weight/volume, based on the solvent system.

In one advantageous modality of the invention, the organic solvent system of the hydrophobic phase consists of at least one ether, one halogenoalkane, one halogenoalkene or one halogenoaromatic compound, or else a mixture thereof.

In practice, the solvent system is preferably chosen from the following compounds:

chlorofluorocarbons and analogs, hydrogenofluorocarbons and analogs, chlorocarbons and analogs,
acetals,
ethers,
esters,
ketones,
alcohols, and
mixtures thereof,
trichlorofluoromethane, dichlorodifluoromethane, 1-chloro-1-difluoroethane, methyl formate, methylal and dimethyl ether being particularly preferred.

In another advantageous modality of the invention, the mass ratio of the hydrophobic organic phase to that of the hydrophilic phase, expressed in part by weight, is set between 100/1 and 1/1, preferably between 50/1 and 1/1 and particularly preferably between 20/1 and 2/1.

The propellant used to ensure vaporization of the composition preferably consists of at least one liquefied or non-liquefied, pressurized gas preferably selected from the following list of products: propane, butane, isobutane, nitrogen, $CO_2$, dimethyl ether, halogenoalkanes (e.g. chlorofluorocarbons or analogs) and mixtures thereof.

To simplify the composition, it is advantageous if at least part of the solvent system acts as both solvent and propellant simultaneously.

In practice, and out of concern for the environment, it is possible to use gases and/or solvents which are not aggressive towards the ozone layer.

The amount of propellant is not an essential datum of the composition of the invention but, as an illustrative indication, it is generally between 1 and 99% by weight/weight, preferably between 40 and 90% by weight/weight, based on the total amount of aerosol.

The hydrophilic phase of the composition is preferably aqueous. In the context of optimization of the aerosol composition of the invention, it has been shown to be of particular value, in certain cases, to incorporate adjuvants into the aqueous phase.

In particular, the presence of $C_1$ to $C_{10}$ lower alcohols, such as ethanol or propanol, is sometimes desirable for improving the solubilization of some of the constituents of the aerosol composition.

Ethanol is preferably selected from among the abovementioned lower alcohols which can be incorporated into the composition.

Certain adjuvants can be useful for increasing the water retention capacity of the preferably hydrated membrane obtained after vaporization of the aerosol composition of the invention. Such functional adjuvants can be chosen from among the known products. According to the invention, it is more preferable to select polyols such as glycerol, glycols, or "polymeric" alcohols such as polyglycols like polyethylene glycol or polypropylene glycol, of variable molecular weights.

The concentrations of these adjuvants in the composition are advantageously
from 0.1 to 10%, preferably from 0.5 to 5%, in the case of lower alcohols, and
from 0 to 50%, preferably 5 to 10%, in the case of polymeric alcohols.

To perfect the therapeutic efficacy of the aerosol composition of the invention in its application as a dressing, one or more active principles of a pharmaceutical or cosmetic nature, for example, can be added thereto.

This active ingredient can be e.g. a disinfectant for external use of the known and/or marketed type, a bactericide, fungicide or virucide, an analgesic, an antiinflammatory, a hemostat or any other compound which is useful for preparing drugs for external use.

The active principles can also be of a cosmetic nature, such as sun protection products or even insect repellents.

It should be noted that the abovementioned functional adjuvants can serve to solubilize some of the abovementioned active principles.

In a preferred mode of carrying out the invention:
the hydrophobic organic phase of the composition comprises
a polymer of leucine and/or of a glutamic acid alkyl ester, and
a solvent consisting of a pressurized mixture of dimethyl ether and methylal, which also acts as propellant,
while its hydrophilic phase contains water, and
a polyol, preferably a polyethylene glycol,
said composition optionally containing one or more of the active principles referred to above.

It is self-evident that various other products or excipients traditionally employed in aerosol compositions can be added to this composition.

This aerosol composition is prepared in conventional manner by bringing together the polymer and the solvent and then incorporating the aqueous phase and the propellant gas under pressure. The container used is a conventional aerosol can crimped just before injection of the liquid propellant gas under pressure.

The vaporization of this composition, which is preferably emulsified beforehand by shaking, takes place in conventional manner by the formation of a mist of microdroplets of variable size. In one variant, and by extrapolation, the vaporization can be compared to a shot of liquid.

According to another of its aspects, the invention relates to the preferably hydrated membrane obtained by vaporization of the aerosol composition described above. It is clear that the aerosol composition is perfectly suitable and appropriate for the formation of a hydrated film, but it is perfectly possible to envisage producing this film from a foam or a cream.

The film obtained by vaporization is advantageously flexible and moist. This moisture is preferably obtained at least partly by hydration. The hydration time depends on the one hand on the water evaporation rate, an unavoidable phenomenon at room temperature, and on the other hand on the water retention capacity of the membrane, which, as has been seen, can be adjusted with the aid of functional adjuvants like polyethylene glycol.

Industrial Application

Apart from application as a dressing (wounds, burns, dermatology, treatment of sunstroke, etc.), the composition according to the invention can find valuable outlets particularly in the fields of the controlled release of active principles (transdermal systems) and the surface treatment of biomaterials (to render them biocompatible).

The present invention will be understood more clearly and its advantages and practical variants will become apparent from the following Examples describing the preparation of aerosol compositions and the production of preferably hydrated dressings by vaporization.

EXAMPLES

General Considerations

In the Examples which follow, the aerosol composition according to the invention is prepared by bringing the polymer Leu/Glu(OMe) into contact with a liquefied gas under pressure. The addition of polyethylene glycol (PEG) and water (or only one of the two) leads to the formation of a fluid emulsion which can readily be vaporized. This emulsion separates in a few hours but a homogeneous mixture is restored by shaking the can. It is not necessary to add surfactants in order to obtain this effect. During vaporization, part of the solvent system evaporates and the treated surface is covered with a continuous, thin film (about 30 μm), which is of variable moisture content and transparency depending on the exact composition of the formulation. After about 60 seconds, the film is sufficiently solid to be lifted and repositioned. When used as a dressing, this film adheres sufficiently well to the skin and is removed easily, and also painlessly, under a stream of water.

Example 1

1. 0.35 g of copolymer Leu/Glu(OMe) of molar composition 49/51 and of reduced viscosity 0.8 dl/g is weighed out.
2. 27 ml of freon 11 and 1.3 ml of ethanol are added and the mixture is shaken until all the polymer has dissolved. This gives a viscous and slightly opaque solution.
3. The solution is diluted by the addition of 18 ml of freon 11.
4. 4.6 g of water and 7.6 g of PEG 600 are added to the polymer solution and the aerosol can is crimped and shaken to form the emulsion.
5. 42 g of freon 22 are injected under pressure and the can is shaken.

A hydrated, flexible and transparent film is obtained after spraying.

Example 2

Procedure according to Example 1, the copolymer being a copolymer Leu/Glu(OMe) 47/53 of reduced viscosity 1.9 dl/g. A hydrated, flexible and transparent film is obtained.

Example 3

Procedure according to Example 1 but without the addition of water. A flexible and transparent membrane is obtained.

Example 4

1.01 g of polymer Leu/Glu(OMe) of molar composition 47/53 and of reduced viscosity 2.0 dl/g are weighed out. 20.26 g of methyl formate and 0.7 g of PEG 600 are added. The aerosol valve is crimped on and the can is shaken until dissolution is complete. 13.76 g of standard butane/isobutane/propane mixture are then injected (2.5 bar). A continuous, flexible and strong film is obtained after spraying onto the skin.

Example 5

0.81 g of polymer Leu/Glu(OMe) of molar composition 47/53 and of reduced viscosity 2.0 dl/g is weighed out. 14.94 g of methylal (dimethoxymethane) are added and the aerosol valve is crimped on. After shaking until dissolution is complete, 30 g of dimethyl ether are injected, followed by 4.20 g of a PEG 600/water mixture of composition 63/37% w/w. A continuous, flexible and hydrated film is obtained after spraying onto the skin.

Example 6

1.01 g of polymer Leu/Glu(OMe) of molar composition 47/53 and of reduced viscosity 2.0 dl/g are weighed out. 20.26 g of methyl formate and 0.70 g of PEG 600 are added. The aerosol valve is crimped on. After shaking until dissolution is complete, 13.76 g of a butane/isobutane/propane mixture are injected under pressure (2.5 bar). A continuous and flexible film is obtained after spraying onto the skin.

What is claimed is:

1. An aerosol composition for forming a membrane after vaporization, comprising
   at least one hydrophobic phase containing at least one hydrophobic polyamino acid which is at least partially solubilized in an organic solvent system,
   at least one hydrophilic phase, and
   at least one propellant wherein:
   (i) the hydrophobic amino acid in the polyamino acid is present in at least 5% by number;
   (ii) the polyaminoacids have a molecular weight of $10^3$ to $15 \times 10^5$ D;
   (iii) the polyaminoacids are present in an amount of 0.05–30% (w/w), based on the total amount of the aerosol;
   (iv) the polyaminoacids are present in the hydrophobic phase in an amount of 0.1–40% (w/v), based on the solvent system;
   (v) the hydrophobic organic phase and the hydrophilic phase have a mass ratio of 100:1 to 1:1;
   (vi) the propellant comprises at least one liquefied or non-liquefied, pressurized gas; and
   (vii) the propellant is present in an amount of 1–99% (w/w) based on the total amount of aerosol.

2. A composition according to claim 1 devoid of water and comprising:
   in its hydrophobic organic phase:
      a polymer of leucine and/or of a glutamic acid alkyl ester, and
      a solvent selected from the group consisting of dimethyl ether, methylol, methyl formate and mixtures thereof,
   in its hydrophilic phase:
      polyethylenglycol, polypropyleneglycol or a mixture thereof;
   a propellant;
   and optionally one or more active principles.

3. A composition according to claim 1 wherein the solvent system comprises
   at least one compound selected from the class of ethers and/or halogenoalkanes and/or halogenoalkenes and/or halogenoaromatic compounds.

4. A composition according to claim 1 wherein the propellant is a pressurized gas.

5. A composition according to claim 1 wherein the aqueous phase contains aduvants.

6. A composition according to claim 1 wherein at least one, active principle is added thereto.

7. A composition according to claim 1 wherein
   its hydrophobic organic phase comprises
      a polymer of leucine and/or of a glutamic acid alkyl ester, and
      a solvent consisting of a pressurized mixture of dimethyl ether and methylal, which also acts as propellant,
   its hydrophilic phase contains
      water, and
      a polyol, and
   it optionally contains one or more active principles.

8. A membrane which it is obtained by vaporization of the aerosol composition according to claim 1.

9. Application of the composition according to claim 1, as a dressing, as a transdermal system for the controlled release of active principles or in the surface treatment of biomaterials.

10. Application of the membrane according to claim 8 as a dressing, as a transdermal system for the controlled release of active principles, or in the surface treatment of biomaterials.

11. A composition according to claim 1 wherein the membrane is hydrated.

12. A composition according to claim 1 wherein the polyamino acid is composed of amino acid selected from the group consisting of alanine, valine, leucine, isoleucine, proline, methionine, phenylalanine, tryptophan, aspartic acid esters, glutamic acid esters, and mixtures thereof.

13. A composition according to claim 1 wherein the hydrophilic phase is aqueous.

14. A composition according to claim 1 wherein the content of hydrophobic amino acids in the polyamino acid is greater than or equal to 15% by number.

15. A composition according to claim 1 wherein the concentration of the polymer in the hydrophobic organic phase is between 0.5 and 10% by weight/volume.

16. A composition according to claim 1 wherein the concentration of the polymer in the hydrophobic organic phase is between 0.5 and 4% by weight/volume.

17. A composition according to claim 1 wherein the solvent system comprises at least one compound selected from the class of ethers and/or halogenoalkanes and/or halogenoalkenes and/or halogenoaromatic compounds, and at least one chlorofluorocarbon or analog, one hydrogenofluorocarbon or analog, one chlorocarbon or analog, one acetal, one ether, one ester, one ketone, one alcohol or a mixture thereof.

18. A composition according to claim 1 wherein the solvent system comprises trichlorofluoromethane, dichlorofluoromethane, 1-chloro-1-difluoroethane, methylformate, methylal, dimethyl ether or a mixture thereof.

19. A composition according to claim 5, wherein the pressurized gas is selected from the group consisting of propane, butane, isobutane, nitrogen, $CO_2$, dimethyl ether, halogenoalkanes and mixtures thereof.

20. A composition according to claim 5 wherein the adjuvants are alcohols.

21. A composition according to claim 5 wherein the adjuvants are selected from the group consisting of ethanol, propanol, glycols, polyglycols, polyols and mixtures thereof.

22. A composition according to claim 1 wherein the mass ratio of hydrophobic organic phase to hydrophilic phase, expressed in parts by weight, is between 50/1 and 1/1.

23. A composition according to claim 1 wherein the mass ratio of hydrophobic organic phase to hydrophilic phase, expressed in parts by weight, is between 20/1 and 2/1.

24. A composition according to claim 6 wherein the active principle is a pharmaceutical or cosmetic ingredient.

25. A composition according to claim 7 wherein the polyol is a polyethylene glycol.

26. A composition according to claim 1 wherein the propellant is selected from the group consisting of propane, butane, isobutane, nitrogen, $CO_2$, dimethyl ether, halogenoalkanes and mixtures thereof.

27. A composition according to claim 24, wherein the active principle is selected from the group consisting of disinfectants, bactericides, fungicides, virucides, analgesics, anti-inflammatories, hemostats, sun protection products, insect repellents, and mixtures thereof.

28. A membrane according to claim 8 which is hydrated.

29. An application as claimed in claim 10 wherein the membrane is hydrated.

30. An aerosol composition for forming a membrane after vaporization comprising:

at lease one hydrophobic phase containing at least one hydrophobic polyamino acid which is at least partially solubilized in an organic solvent system, at least one hydrophilic phase, wherein (I) the hydrophobic amino acid in the polyamino acid is present in at least 5% by number;

(ii) the polyaminoacids have a molecular weight of $10^3$ to $15\times10^5$D;

(iii) the polyaminoacids are present in an amount of 0.05–30% (w/w), based on the total amount of the aerosol;

(iv) the polyaminoacids are present in the hydrophobic phase in an amount of 0.1–40% (w/v), based on the solvent system;

(v) the hydrophobic organic phase and the hydrophilic phase have a mass ratio of 100:1 to 1:1.

31. A composition according to claim 30 comprising water.

32. A composition according to claim 30 wherein the hydrophilic phase contains water.

33. A composition according to claim 30 which does not comprise water.

34. A composition according to claim 30 wherein at least part of the solvent system acts as both solvent and propellant simultaneously.

35. A composition according to claim 30 wherein the solvent system at least one compound selected from the group consisting of ethers, halogenoalkanes, halogenoalkenes, halogenoaromatic compounds and mixtures thereof.

36. A composition according to claim 30 wherein at least part of the solvent system acts as both solvent and propellant simultaneously.

37. A composition according to claim 30 wherein the aqueous phase contains adjuvants.

38. A composition according to claim 30 wherein at least one active principle is added thereto.

39. A composition according to claim 30 wherein:

its hydrophobic organic phase comprises a polymer of leucine and/or of a glutamic acid alkyl ester, and a solvent consisting of a pressurized mixture of dimethyl ether and methylal, which also acts as propellant, its hydrophilic phase contains water, and a polyol, and it optionally contains one or more active principles.

40. A membrane that it is obtained by vaporization of the aerosol composition according to claim 30.

41. A method for the surface treatment of biomaterials which comprises applying the composition according to claim 30 as a transdermal system for the controlled release of active principles for the surface treatment of biomaterials.

42. A method of dressing by applying the membrane according to claim 40 as a dressing, as a transdermal system for the controlled release of active principles, or in the surface treatment of biomaterials.

43. A composition according to claim 30 wherein the membrane is hydrated.

44. A composition according to claim 30 wherein the polyamino acid is obtained from alanine, valine, leucine, isoleucine, proline, methionine, phenylalanine, tryptophan, aspartic acid esters, glutamic acid esters, or mixtures thereof.

45. A composition according to claim 30 wherein the content of hydrophobic amino acids in the polyamino acid is greater than or equal to 15% by number.

46. A composition according to claim 30 wherein the concentration of the polymer in the hydrophobic organic phase is between 0.5 and 10% by weight/volume.

47. A composition according to claim 30 wherein the concentration of the polymer in the hydrophobic organic phase is between 0.5 and 4% by weight/volume.

48. A composition according to claim 30 wherein the solvent system comprises:

at least one compound selected from the group consisting of ethers, halogenoalkanese, halogenoalkenes, halogenoaromatic compounds and mixtures thereof, and at least one chlorofluorocarbon or analog, one hydrogenofluorocarbon or analog, one chlorocarbon or analog, one acetal, one ether, one ester, one ketone, one alcohol or a mixture thereof.

49. A composition according to claim 30 wherein the solvent system comprises trichlorofluoromethane, dichlorofluoromethane, 1-chloro-1-difluoroethane, methylformate, methylal, dimethyl ether or a mixture thereof.

50. A composition according to claim 37 wherein the adjuvants are alcohols.

51. A composition according to claim 37 wherein the adjuvants are selected from the group consisting of ethanol, propanol, glycols, polyglycols, polyols and mixtures thereof.

52. A composition according to claim 30 wherein the mass ratio of hydrophobic organic phase to hydrophilic phase, expressed in parts by weight, is between 50/1 and 1/1.

53. A composition according to claim 30 wherein the mass ratio of hydrophobic organic phase to hydrophilic phase, expressed in parts by weight, is between 20/1 and 2/1.

54. A composition according to claim 38 wherein the active principle is a pharmaceutical or cosmetic ingredient.

55. A composition according to claim 39 wherein the polyol is a polyethylene glycol.

56. A composition according to claim 30 wherein the propellant is selected from the group consisting of propane, butane, isobutane, nitrogen, $CO_2$, dimethyl ether, halogenoalkanes and mixtures thereof.

57. A composition according to claim 54, wherein the active principle is selected from the group consisting of disinfectants, bactericides, fungicides, virucides, analgesics, anti-inflammatories, hemostats, sun protection products, insect repellents, and mixtures thereof.

* * * * *